United States Patent [19]

McGredy

[11] Patent Number: Plant 7,031

[45] Date of Patent: Sep. 19, 1989

[54] ROSE PLANT NAMED BABY SUNRISE

[76] Inventor: Samuel D. McGredy, 130 B Beach Road, Castor Bay, Auckland 9, New Zealand

[21] Appl. No.: 102,549

[22] Filed: Feb. 29, 1988

[51] Int. Cl.[4] ..... A01H 5/00

[52] U.S. Cl. ..... Plt./7

[58] Field of Search ..... Plt. 7

*Primary Examiner*—Robert E. Bagwill

[57] ABSTRACT

A new miniature rose variety of orange and yellow blending.

1 Drawing Sheet

The following is a detailed description of my new variety, with color terminology in accordance with The Royal Horticultural Society Colour Chart (RHSCC). The terminology used in color description herein refers to plate numbers in the aforementioned color chart, "137B" is plane 137B of The Royal Horticultural Society Colour Chart.

Parentage: Seedling.
Seed parent: "Dorola".
Pollen parent: "Moana".
Class: Miniature.
Name: "Baby Sunrise".

The following observations are made of specimens grown outdoors in Washington County, Oreg. during July.

FLOWER

Blooming Habit: Near continuous.

A. Bud:
- (1) *Size.*—Small, about 1 cm.
- (2) *Form.*—Pointed.
- (3) *Color.*—When sepals first divide you see the reverse of the petals — a solid yellow color.
- (4) *Sepals.*—Spear shaped, reflexed, ⅓ cm longer than bud length.
- (5) *Peduncle.*—Length — About 2 cm. Aspect — straight. Strength — erect. Color — near 137c green.

B. Bloom:
- (1) *Size.*—Average size when fully expanded — about 2½ cm.
- (2) *Borne.*—Singles and sprays.
- (3) *Form.*—Informal, decorative, smooth petals opening outward becoming a double bloom.
- (4) *Petalage.*—Number of petals under normal condition — 34.
- (5) *Color.*—After sepals fall, visible bud coloring is yellow, color 20B on reverse petals and showing gold base 16B. The inner petals are orange, color 29A, on outer half, blending to yellow, 20B, toward the center. The inner petal base is gold, 16B involving ⅓ of the petal. As the bloom ages the gold base center matures to yellow and the orange outer petals mature to pink orange. This occurs in about five days.

C. Petals
- (1) *Texture.*—Moderately thick and of good substance.

- (2) *Appearance.*—Inside — velvety, outside velvety.
- (3) *Form.*—The bloom has imbricated form and reflexes. Outer petals are pointed with smooth edge, inner petals also pointed.
- (4) *Arrangement.*—Regularly arranged.
- (5) *Petaloids in center.*—Medium, surrounding center.
- (6) *Persistence.*—Drop off cleanly.
- (7) *Fragrance.*—Light.
- (8) *Lasting quality.*—Very long lasting on plant and blooms last 6 days as cut flower.

REPRODUCTIVE ORGANS

A. Stamens, filaments and anthers:
- (1) *Arrangement.*—Regularly arranged stamens around low pistils.
- (2) *Color.*—Medium yellow.

B. Pollen:
- *Color.*—Yellow.

C. Styles: Even length, introse.

D. Stigmas:
- *Color.*—Medium Yellow.

E. Hips: Usually do not form.

F. Sepals: Permanent, spear shaped, reflexed.

PLANT

A. Form: Rounded, dwarf.

B. Growth: Uniform branching, medium vigor.
- *Height attained.*—About 27 cm.

C. Foliage: Compound 5 leaflets.
- (1) *Size.*—Medium, ¾ cm leaflets.
- (2) *Quantity.*—Abundant.
- (3) *Color.*—New foliage: Upper side — near to 137B. Under side — near to 138B. Old foliage: Upper side — Near 137B. Under side — near 138B.
- (4) *Shape.*—Oval pointed, supported by short petiolule.
- (5) *Texture.*—Upper side is matte.
- (6) *Edge.*—Serrated.
- (7) *Serration.*—Serrulate.
- (8) *Leaf stem.*—Color — Lt green 137B, turning green 138B.
- (9) *Stipules.*—Slightly bearded, and ⅓ cm.
- (10) *Rachis.*—Green color, Medium — ½ cm upper side and grooved.
- (11) *Resistance to disease.*—Blackspot — Average. Mildew — Average. Rust — Average.

D. Wood:

(1) *New wood.*—Color — Light green near 137B. Bark — smooth.

(2) *Old wood.*—Color — near 138B. Bark — smooth, with sturdy growth with 1 cm internodes.

E. Thorns:

(1) *Thorns.*—Quantity (main stalk) — average. On laterals from stalk — average. Form — needle, declining. Length — $\frac{1}{3}$ cm. Color — cream turning to light brown. Position — ordinary.

(2) *Prickles.*—Average.

F. Winter hardiness: Requires ordinary protection in extreme climates.

The drawings show blossoms and foliage of my new variety.

The new variety has been reproduced by budding and cuttings.

I claim:

1. The present invention relates to a new and distinct variety of rose plant of the miniature rose class, which was originated by crossing as seed parent the rose known as "Dorola" and as pollen parent the rose known as "Moana".

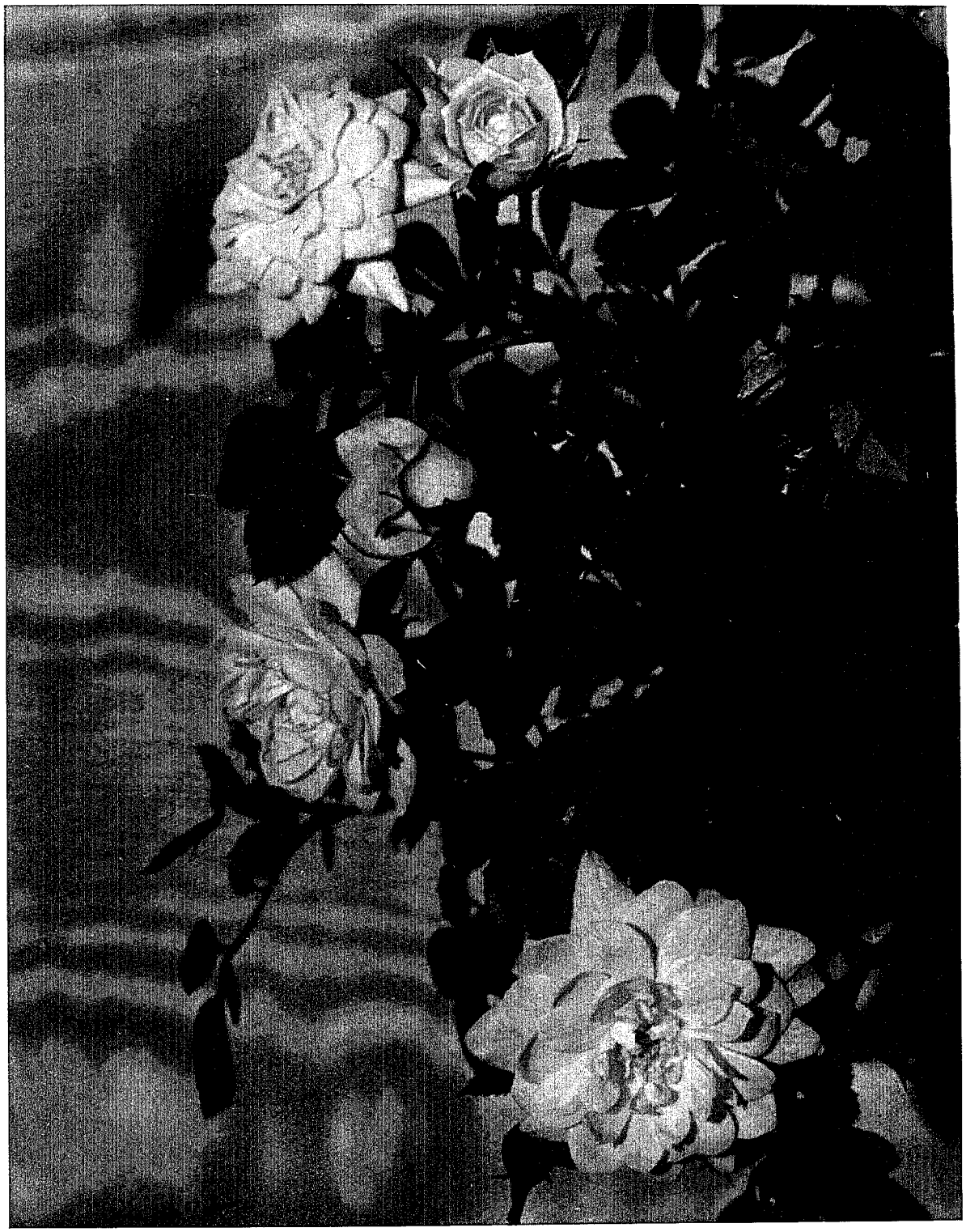

* * * * *